United States Patent [19]

Katoh et al.

[11] Patent Number: 4,581,326
[45] Date of Patent: Apr. 8, 1986

[54] SILVER HALIDE COLOR PHOTOGRAPHIC MATERIAL

[75] Inventors: Katsunori Katoh; Satoshi Kawakatsu, both of Hachioji; Kosaku Masuda, Akishima; Kaoru Miyagi, Tachikawa; Noritaka Nakayama, Hachioji; Toshihiko Kimura, Hino, all of Japan

[73] Assignee: Konishiroku Photo Industry Co., Ltd., Japan

[21] Appl. No.: 648,038

[22] Filed: Sep. 6, 1984

[30] Foreign Application Priority Data

Sep. 9, 1983 [JP] Japan .................. 58-167236

[51] Int. Cl.$^4$ .................. G03C 7/26
[52] U.S. Cl. .................. 430/551; 430/558
[58] Field of Search .................. 430/551, 558

[56] References Cited

U.S. PATENT DOCUMENTS

| | | | |
|---|---|---|---|
| 3,725,067 | 4/1973 | Bailey et al. | 430/558 |
| 4,338,393 | 7/1982 | Bailey et al. | 430/548 |
| 4,443,536 | 4/1984 | Lesting | 430/558 |
| 4,489,155 | 12/1984 | Sakanoue et al. | 430/551 |
| 4,500,630 | 2/1985 | Sato et al. | 430/558 |
| 4,513,082 | 4/1985 | Furutachi et al. | 430/552 |
| 4,526,864 | 7/1985 | Takada et al. | 430/551 |

Primary Examiner—J. Travis Brown
Attorney, Agent, or Firm—Finnegan, Henderson, Farabow, Garrett, & Dunner

[57] ABSTRACT

A silver halide color photographic material is disclosed which has at least one silver halide emulsion layer on a support, said silver halide emulsion layer containing at least one magenta coupler of formula (I) and at least one non-color forming phenolic compound:

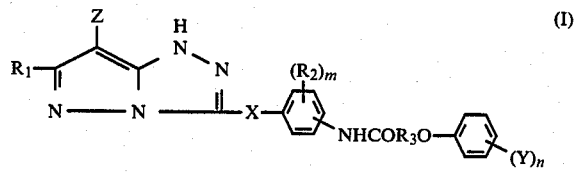

wherein $R_1$ is an alkyl or aryl group; $R_2$ is a monovalent group; $R_3$ is an alkylene group; Y is a halogen atom, a hydroxy or alkyl group; Z is a group that can be eliminated upon coupling reaction with the oxidized product of a color developing agent; X is a divalent bonding group or an alkylene group having 1 to 5 carbon atoms; m is an integer of 0 to 4; and n is an integer of 0 to 5.

8 Claims, No Drawings

SILVER HALIDE COLOR PHOTOGRAPHIC MATERIAL

FIELD OF THE INVENTION

The present invention relates to a silver halide color photographic material which features an increased sensitivity, good image quality and decreased silver deposit.

BACKGROUND OF THE INVENTION

In color photography, images are produced by a color dye which is formed by the coupling reaction between the oxidized product of an aromatic primary amine color developing agent and a coupler. With multi-color photographic elements, a color image is usually produced by the subtractive color process, and the dye formed by the coupling reaction is typically a cyan, magenta or yellow dye which is produced in a silver halide emulsion layer or a layer adjacent thereto, said silver halide emulsion layer having sensitivity to the wavelength region of specific light to be absorbed by the image forming dye, namely, the red, green or blue region of the spectrum.

Pyrazolone couplers are commonly used as the magenta dye forming coupler, but they have low maximum color density and sensitivity, and absorptions other than the predominant one which are undesired. Furthermore, these couplers do not have sufficient long-term stability, and in particular, they are low in resistance to formalin and experience appreciable change in color and decrease in color formability.

In order to eliminate these defects, several proposals have been made. Japanese Patent Publication No. 30895/1973 shows a 1H-pyrazolo(3,2-c)-s-triazole magenta coupler having no undesired absorption other than the predominant one. However, with this coupler, little improvement has been achieved with respect to maximum color density, sensitivity and resistance to formalin.

Japanese Patent Publication No. 16058/1974 shows a bis-pyrazolone magenta coupler. This coupler has some improvement in sensitivity and formalin resistance, but not in maximum color density. Japanese Patent Public Disclosure No. 135841/1981 shows a 1H-pyrazolo(3,2-c)-s-trizole magenta coupler having its 1-position substituted by an active point in a compound having an active methylene group. This coupler is somewhat improved in formalin resistance, but not in maximum color density or sensitivity. Japanese Patent Public Disclosure No. 42045/1983 shows the use of a coupler having a terminal hydroxyphenylene sulfonyl group for the purpose of providing an improved maximum color density. However, the obtained maximum color density is not as high as desired.

SUMMARY OF THE INVENTION

One object of the present invention is to provide a silver halide color photographic material which has high sensitivity and forms a magenta dye exhibiting high color density.

Another object of the present invention is to provide a silver halide color photographic material forming a magenta dye which has high storage stability, particularly in the presence of an air contaminant such as formalin.

Still another object of the present invention is to provide a silver halide color photographic material forming a magenta dye which does not have any absorption other than the principal absorption that is undesired.

A further object of the present invention is to provide a silver halide color photographic material forming a magenta dye which permits the use of less silver than is conventionally required and which therefore complies with the purpose of saving precious silver resources.

A still further object of the present invention is to provide a silver halide color photographic material forming a magenta dye which permits the reduction in the thickness of a silver halide emulsion layer and which provides an image of improved quality such as sharpness.

Therefore, in order to achieve the objects stated above, the present inventors made various studies in search for a silver halide color photographic material that uses a novel photographic magenta coupler and which achieves a higher sensitivity, provides an image of better quality and uses less silver than is conventionally required. As a result, it has been found that the objects stated above of the present invention can be accomplished by a silver halide color photographic material having at least one silver halide emulsion layer on a support, said silver halide emulsion layer containing at least one magenta coupler of formula (I) and at least one non-color forming phenolic compound (hereunder referred to as the phenolic compound of the present invention):

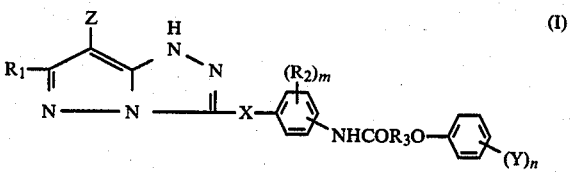

(I)

wherein $R_1$ is an alkyl or aryl group; $R_2$ is a monovalent group; $R_3$ is an alkylene group; Y is a halogen atom, a hydroxy or alkyl group; Z is a group that can be eliminated upon coupling reaction with the oxidized product of a color developing agent; X is a divalent bonding group or an alkylene group having 1 to 5 carbon atoms; m is an integer of 0 to 4; and n is an integer of 0 to 5.

DETAILED DESCRIPTION OF THE INVENTION

In the silver halide color photographic material of the present invention, in order to accomplish the objects of the present invention, it is necessary that a magenta coupler represented by formula (I) and a non-color forming phenolic compound according to the present invention be incorporated in the same silver halide emulsion layer.

In formula (I), $R_1$ represents an alkyl or aryl group, and the alkyl group is preferred. Preferred alkyl groups are those having 1 to 8 carbon atoms. More preferred alkyls are those having 1 to 4 carbon atoms, such as methyl, ethyl, ethoxyethyl and t-butyl.

A preferred aryl group represented by $R_1$ is a phenyl group which may be substituted as in p-methoxyphenyl, m-chlorophenyl or p-(t)-butylphenyl.

The symbol $R_2$ represents a monovalent group such as a halogen atom (e.g. chlorine), an alkoxy group (e.g. methoxy or t-butoxy), an alkyl group (e.g. methyl, ethyl, methoxyethyl or benzyl), a nitro group, or a cyano group.

The symbol $R_3$ represents an alkylene group such as methylene, 1,1-ethylene, 1,3-propylene, 1,1-nonylene, 1,1-dodecylene or 1,1-tridecylene.

A preferred halogen atom represented by Y is a chlorine atom. A preferred alkyl group represented by Y is selected from among those having 1 to 20 carbon atoms, such as methyl, ethyl, t-butyl, t-amyl, t-octyl, n-dodecyl and n-pentadecyl.

The group represented by Z which can be eliminated upon coupling reaction with the oxidized product of a color developing agent means a "split-off" group present in conventional two-equivalent couplers, and does not include a hydrogen atom. Specific examples of this split-off group include a halogen atom (e.g. chlorine or fluorine), an aryloxy group (e.g. phenoxy, p-methoxyphenoxy, p-butanesulfonamidophenoxy, or p-tert-butylcarboamidophenoxy), an arylthio group (e.g. phenylthio) and a heterocyclic thio group (e.g. 1-ethyltetrazole-5-thioyl). A halogen atom is preferred, and a chlorine atom is particularly preferred.

m represents an integer of 0 to 4, preferably 0; n represents an integar of 0 to 5, preferably 1 to 3. When n is 2 or more, Y may be the same or different groups. The group

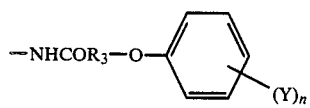

in formula (I) represents a ballast group sufficient to render non-diffusible the photographic magenta coupler of formula (I). When Y is an alkyl group, the sum of the carbon atoms in the alkylene group ($R_3$) and alkyl group (Y) is preferably in the range of 8 to 30, more preferably from 12 to 25. When n is 0, or when n is an integer of 1 to 3 and Y is selected from among a halogen atom and a hydroxyl group, the alkylene group represented by $R_3$ preferably has 8 to 20 carbon atoms.

The alkylene group having 1 to 5 carbon atoms represented by "X" may be a straight chain alkylene group or a branched alkylene group.

The phenolic compound of the present invention is preferably non-diffusible. This is because the objects of the present invention can be effectively achieved when this phenolic compound and the magenta coupler of formula (I) of the present invention are present in the same silver halide emulsion layer and if said phenolic compound has non-diffusible nature.

The phenolic compound of the present invention may be selected from among any of the non-color forming compounds which are preferably non-diffusible. For example, known phenolic high-boiling organic solvents commonly used for preparing coupler dispersions may be used.

Preferred phenolic compounds of the present invention are those which have melting points not higher than 50° C. and which are solid at normal temperature (25° C.), or those which are liquid at normal temperature and which have boiling points higher than 200° C. at normal pressure (one atmosphere).

The phenolic compound of the present invention preferably has a group for imparting the non-diffusible nature.

Preferred phenolic compounds of the present invention are represented by the following formula (II):

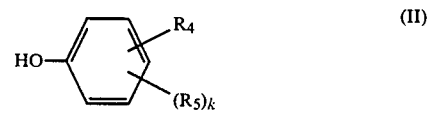

wherein $R_4$ and $R_5$ are each a halogen atom, an alkyl group, a cycloalkyl group or an alkoxy group; k is an integer of 0 to 4, provided that when k is 2 or more, $R_5$ may be the same or different groups.

In formula (II), the halogen atom represented by $R_4$ or $R_5$ is preferably a chlorine atom; the alkyl group represented by $R_4$ or $R_5$ preferably has 1 to 20 carbon atoms, and suitable examples are substituted or unsubstituted straight- or branched-chain alkyl groups such as methyl, ethyl, phenetyl, 2-(p-phydroxyphenyl)propane-2-yl, 1-(p-hydroxyphenyl)butane-1-yl, iso-propyl, butyl, tert-butyl, amyl, sec-amyl, tert-amyl, hexyl, octyl, tert-octyl, decyl, dodecyl, and 8-hexadecenyl; the cycloalkyl group represented by $R_4$ or $R_5$ is preferably a cyclohexyl group; the alkoxy group represented by $R_4$ or $R_5$ preferably has 1 to 20 carbon atoms and suitable examples include methoxy, ethoxy, iso-propoxy, tert-butoxy, phenetyloxy, ethoxyethyloxy, octyloxy, nonyloxy, decyloxy, dodecyloxy and octadecyloxy groups.

In formula (II), k represents an integer of 0 to 4, preferably 0 to 3, and the number 0 or 1 is particularly preferred.

In formula (II), the alkyl group, cycloalkyl group or alkoxy group represented by $R_4$ or $R_5$ is preferably a group which is capable of rendering the phenol non-diffusible either alone or in combination with $R_5$ or $R_4$. The total number of the carbon atoms in $R_4$ and $R_5$ is preferably 6 to 30, with the range of 8 to 25 being particularly preferred.

Typical examples of the magenta coupler of the present invention are listed below, but it should be understood that the scope of the present invention is by no means limited to these examples.

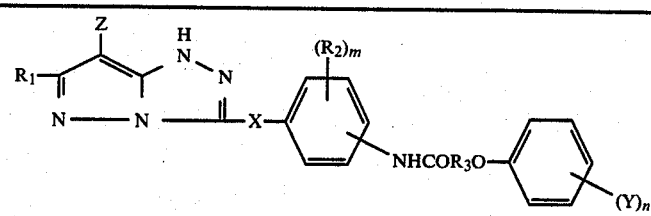

| Coupler No. | R₁ | Z | X | (R₂)ₘ / NHCO- aryl | R₃ | (Y)ₙ aryl |
|---|---|---|---|---|---|---|
| M-1 | CH₃— | Cl— | —(CH₂)₃— | —C₆H₄—NHCO— | —CH₂— | 2,4-di-C₅H₁₁(t)-C₆H₃— |
| M-2 | CH₃— | Cl | —(CH₂)₃— | —C₆H₄—NHCO— | —(CH₂)₃— | 2,4-di-C₅H₁₁(t)-C₆H₃— |
| M-3 | CH₃— | Cl | —CH₂— | 2-NHCO—C₆H₄— | —CH₂— | 3-C₁₅H₃₁-C₆H₄— |
| M-4 | CH₃— | Cl | —(CH₂)₂— | —C₆H₄—NHCO— | —(CH₂)₃— | 4-C₁₅H₃₁-C₆H₄— |
| M-5 | CH₃— | Cl | —(CH₂)₂— | 3-Cl, 5-NHCO—C₆H₃— | —CH(C₂H₅)— | 4-C₁₅H₃₁-C₆H₄— |
| M-6 | CH₃— | Cl | —(CH₂)₃— | —C₆H₄—NHCO— | —CH(C₂H₅)— | 2,4-di-C₅H₁₁(t)-C₆H₃— |
| M-7 | CH₃— | Cl | —(CH₂)₃— | —C₆H₄—NHCO— | —CH(C₁₂H₂₅)— | 2-OH, 6-C₄H₉(t)-C₆H₃— |
| M-8 | C₆H₅— | Cl | —(CH₂)₂— | 3-Cl, 5-NHCO—C₆H₃— | —CH(C₁₀H₂₁)— | 2-OH, 6-C₄H₉(t)-C₆H₃— |
| M-9 | CH₃— | 4-CH₃O-C₆H₄—O— | —(CH₂)₃— | —C₆H₄—NHCO— | —CH(C₄H₉)— | 2,4-di-C₅H₁₁(t)-C₆H₃— |
| M-10 | CH₃— | F | —(CH₂)₂— | 3-OCH₃, 5-NHCO—C₆H₃— | —CH(C₃H₇(iso))— | 2,4-di-C₅H₁₁(t)-C₆H₃— |
| M-11 | CH₃— | Cl | —(CH₂)₃— | —C₆H₄—NHCO— | —CH(C₃H₇(iso))— | 2,4-di-C₅H₁₁(t)-C₆H₃— |

-continued

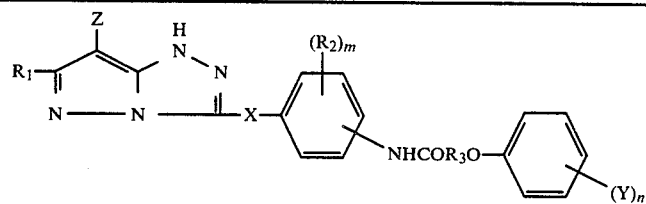

| Coupler No. | R₁ | Z | X | (R₂)ₘ / NHCO— | R₃ | (Y)ₙ |
|---|---|---|---|---|---|---|
| M-12 | phenyl | 1-ethyl-tetrazol-5-ylthio (N—N / N—N—C₂H₅, S—) | —(CH₂)₂— | 4-NHCO—C₆H₄— | —CH₂— | 2,4-di-(t-C₅H₁₁)-C₆H₃— |
| M-13 | CH₃— | 4-methoxyphenoxy (CH₃O—C₆H₄—O—) | —(CH₂)₃— | 4-NHCO—C₆H₄— | —CH(C₁₂H₂₅)— | 3-(t-C₄H₉)-4-OH-C₆H₃— |
| M-14 | CH₃— | Cl | —(CH₂)₂— | 2-C₂H₅, 3-NHCO—C₆H₃— | —CH(C₂H₅)— | 2,4-di-(t-C₅H₁₁)-C₆H₃— |
| M-15 | CH₃— | Cl | —(CH₂)₂— | 3-CN, 5-NHCO—C₆H₃— | —CH(C₆H₁₃)— | 4-C₁₅H₃₁-C₆H₄— |
| M-16 | CH₃— | Cl | —(CH₂)₃— | 4-NHCO—C₆H₄— | —CH(C₁₀H₂₁)— | 2,4,6-trichloro-C₆H₂— |
| M-17 | CH₃— | 4-methoxyphenoxy (CH₃O—C₆H₄—O—) | —(CH₂)₃— | 4-NHCO—C₆H₄— | —CH(C₁₂H₂₅)— | 2,4,6-trichloro-C₆H₂— |
| M-18 | phenyl | C₄H₉SO₂NH—C₆H₄—S— | —(CH₂)₂— | 2-NO₂, 4-NHCO—C₆H₃— | —CH(C₂H₅)— | 2,4-di-(t-C₅H₁₁)-C₆H₃— |
| M-19 | CH₃— | Cl | —(CH₂)₃— | 3-NHCO—C₆H₄— | —CH(C₂H₅)— | 2,4-di-(t-C₅H₁₁)-C₆H₃— |
| M-20 | CH₃— | Cl | —(CH₂)₃— | 4-NHCO—C₆H₄— | —C(CH₃)₂— | 2,4-di-(t-C₅H₁₁)-C₆H₃— |
| M-21 | CH₃— | Cl | —CH(CH₃)CH₂— | 4-NHCO—C₆H₄— | —CH(C₂H₅)— | 2,4-di-(t-C₅H₁₁)-C₆H₃— |

-continued
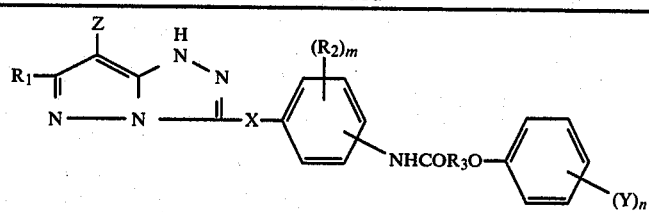
| Coupler No. | $R_1$ | Z | X | (R₂)ₘ—⟨⟩—NHCO— | $R_3$ | —⟨⟩—(Y)ₙ |
|---|---|---|---|---|---|---|
| M-22 | $CH_3-$ | Cl | —CH—<br>    $C_2H_5$ | ⟨⟩—NHCO— | $-(CH_2)_3-$ | ⟨⟩—$C_5H_{11}(t)$<br>    $C_5H_{11}(t)$ |
| M-23 | $CH_3-$ | Cl | — | ⟨⟩<br>NHCO— | —CH—<br>  $C_{12}H_{25}$ | ⟨⟩—OH<br>  $C_4H_9(t)$ |
Typical examples of the phenolic compound of the present invention are listed below, but it should be understood that the scope of the present invention is by no means limited to these examples. Phenolic compounds:
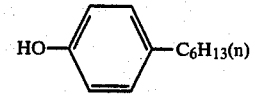 (1)
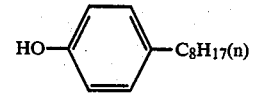 (2)
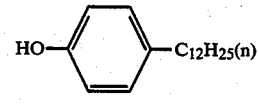 (3)
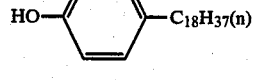 (4)
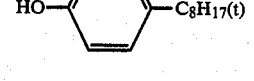 (5)
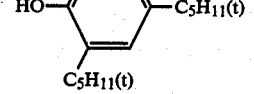 (6)
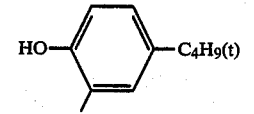 (7)
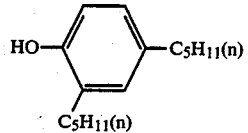 (8)
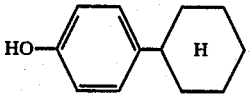 (9)
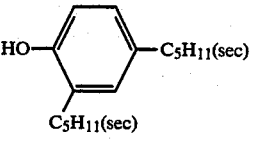 (10)
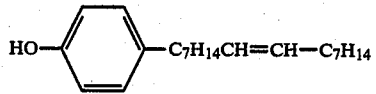 (11)
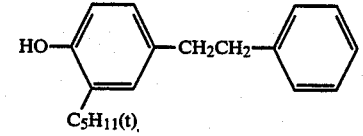 (12)
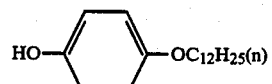 (13)
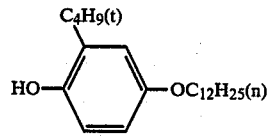 (14)

-continued

(15) 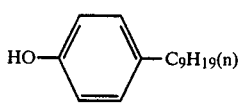

(16) 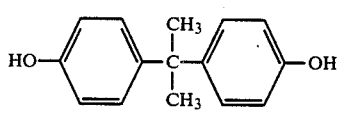

(17) 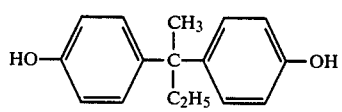

(18)

(19) 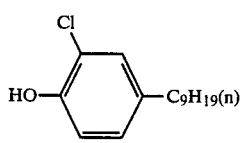

(20)

(21) 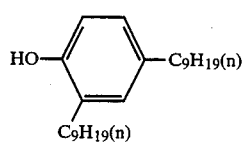

(22) 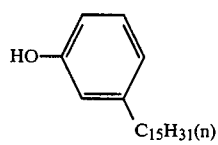

(23) 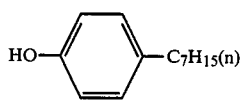

(24) 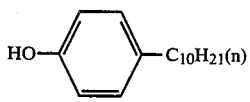

(25) 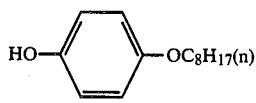

(26) 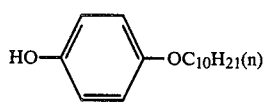

(27) 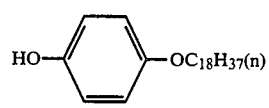

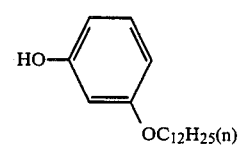

The magenta couplers according to the present invention may be readily synthesized by any of the known methods. A common route of synthesis is depicted below.

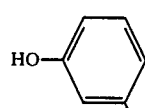

R—COCl ⟶

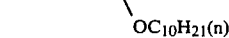

The synthesis of two magenta couplers used in the present invention is shown below.

Synthesis 1: Coupler M-2

To a solution of anhydrous sodium acetate (4.5 g) in acetic acid (150 cc), 6-methyl-3-[3-(p-aminophenyl)-propyl]-1H-pyrazole (3,2-c)-s-triazole (12.7 g) was added at room temperature, and under agitation, γ-(2,4-di-tert-amylphenoxy)-butanoyl chloride (18.6 g) was added in small portions. Following 8-hr agitation, the reaction mixture was poured into water. An oily product formed. It was extracted with ethyl acetate and washed with water. The oily layer was separated and dried with anhydrous magnesium sulfate. After distilling off the solvent under vacuum, the residue was purified by column chromatography on silica gel, and crystallized with ethyl acetate and n-hexane to give a white powder (15.3 g).

Part (11.1 g) of the white powder was uniformly dissolved in chloroform (110 cc), and under cooling with iced water at 10° C.±3° C., a solution of sulfuryl chloride (3.0 g) in chloroform (30 cc) was slowly added dropwise over a period of 1 hr. Following reaction for another one hour at the same temperature, the reaction mixture was poured into water for washing and separating the chloroform layer. It was dried with anhydrous magnesium sulfate and the solvent was distilled off under vacuum. The residue was purified by column chromatography on silica gel and recrystallized with acetonitrile.

A white powder (4.8 g) having mp. 148°–149° C. formed, and its structure was determined by NMR and MASS analyses.

Synthesis 2: Coupler M-7

To a solution of anhydrous sodium acetate (4.5 g) in acetic acid (150 cc), 6-methyl-3-[3-(p-aminophenyl)-propyl]-1H-pyrazole (3,2-c)-s-triazole (12.7 g) was added at room temperature, and under agitation, α-(4-acetyloxy-3-tert-butylphenoxy)tetradecanoyl chloride (25.0 g) was added in small portions. Following 6-hr agitation, the reaction mixture was poured into water. An oily product formed. It was extracted with ethyl acetate and washed with water. The oily layer was separated and dried with anhydrous magnesium sulfate. After distilling off the solvent under vacuum, the residue was purified by column chromatography on silica gel to give a white oil (24.5 g).

Part (20 g) of the white oil was dissolved in chloroform (200 cc), and under cooling with iced water at 10° C.±3° C., a solution of sulfuryl chloride (4.5 g) in chloroform (45 cc) was added dropwise over a period of one hour. Following reaction for another one hour at the same temperature, water was added for washing and separating the chloroform layer. It was dried with anhydrous magnesium sulfate and the solvent was distilled off. The residue was subjected to column chromatography on silica gel to obtain a white oil (8.5 g).

Part (7.1 g) of the white oil was poured into a solution of caustic soda (1.2 g) in a mixture of ethanol (30 cc) and water (30 cc), and the mixture was heated at 40° C.±5° C. for one hour. The reaction mixture was rendered acidic with HCl. An oily product formed. It was extracted with ethyl acetate and washed with water. The oily layer was separated and dried with anhydrous magnesium sulfate. After distilling off the solvent under vacuum, the residue was purified by column chromatography on silica gel and recrystallized from acetonitrile.

A white powder (3.6 g) having mp. 63°–65° C. was obtained and its structure was determined by NMR and MASS analyses.

The silver halide color photographic material prepared by using the magenta coupler specified above may contain any of the conventional dye forming couplers.

Known open-chain ketomethylene compounds may be used as yellow dye forming couplers. Among these, pivaloyl acetanilide and benzoyl acetanilide couplers are useful. Illustrative yellow dye forming couplers are shown in U.S. Pat. No. 2,875,057, British Pat. No. 1,077,874, U.S. Pat. No. 3,408,194, Japanese Patent Public Disclosure Nos. 123342/1975, 87650/1975, and 133329/1979, Japanese Patent Publication No. 19031/1971, Japanese Patent Public Disclosure Nos. 29432/1973, 66834/1973, 66835/1973, 94432/1973, 28834/1975, 99433/1979, 70841/1980, and 74249/1981. Japanese Patent Publication No. 19956/1970, as well as Japanese Patent Public Disclosure Nos. 102636/1976 and 87041/1981.

Suitable cyan dye forming couplers are phenolic and naphtholic compounds. Illustrative cyan dye forming couplers are shown in U.S. Pat. Nos. 2,369,929, 2,474,293, 2,772,162 and 2,895,826, British Pat. No. 1,038,331, Japanese Patent Publication No. 36894/1973, Japanese Patent Public Disclosure No. 21139/1972, U.S. Pat. No. 3,737,316, Japanese Patent Public Disclosure No. 74844/1973, U.S. Pat. Nos. 3,880,661, 4,124,396, and 4,333,999, Japanese Patent Public Disclosure Nos. 21094/1980, 112038/1975, 117422/1975, 18315/1977, 115230/1979, 163537/1980, 136650/1982, 155538/1982, 204545/1982, 32071/1980, 108662/1980. 1938/1981, 27147/1981, 80045/1981 and 104333/1981.

The magenta dye forming couplers defined above according to the present invention may be used either alone or in combination with themselves. If desired, they may be used in combination with known magenta dye forming couplers such as pyrazolone, indazolone, cyanoacetyl, pyrazolinobenzimidazole and pyrazolotriazole compounds. However, it should be emphasized that at least one of the magenta dye forming couplers used in the present invention must be the compound of formula (I).

The phenolic compound of the present invention can be readily synthesized by any of the known methods, such as the one shown in U.S. Pat. No. 2,835,579. Many of the phenolic compounds of the present invention are commercially available, and compounds (3), (5), (6) and (21) listed above are examples of this group.

The magenta coupler according to the present invention is used in a manner similar to that used with conventional magenta and other dye forming couplers. Typically, the magenta coupler of the present invention is incorporated in a silver halide emulsion, which is then applied to a base to form a silver halide color photographic material. The silver halide photographic material may be monochromatic or multi-colored. In the latter case, the magenta coupler of the present invention is usually incorporated in a green-sensitive emulsion, but if desired, the coupler may be incorporated in an unsensitized emulsion layer or an emulsion layer which is sensitive to the primary color regions in the spectrum other than green.

Each of the units that are used in the silver halide color photographic material of the present invention for providing dye images is made of one or more emulsion layers having sensitivity to specified ranges in the spectrum.

The layers necessary for making the silver halide color photographic material including the image forming layers may be arranged in various orders known in the art. A typical multi-colored silver halide photographic material consists of a cyan dye image forming unit comprising at least one red-sensitive silver halide emulsion layer containing at least one cyan dye forming coupler, a magenta dye image forming unit comprising at least one green-sensitive silver halide emulsion layer containing at least one magenta dye forming coupler as defined in the present invention, and a yellow dye image forming unit comprising at least one blue-sensitive silver halide emulsion layer containing at least one yellow dye forming coupler, with these three image forming units carried on a support.

The photographic material according to the present invention may contain additional layers such as a filter layer, an intermediate layer, a protective layer and a subbing layer.

The magenta coupler and non-color forming phenolic compound according to the present invention may be incorporated in a silver halide photographic material by any of the known methods. For example, the magenta coupler and non-color forming phenolic compound according to the present invention are dissolved in a mixture of a known high-boiling solvent and a low-boiling solvent such as butyl acetate or butyl propionate; the solution is then mixed with an aqueous solution of gelatin containing a surfactant; the mixture is emulsified with a high-speed rotary mixer, colloid mill or an ultrasonic disperser, and the resulting emulsion is added to a separately prepared silver halide, thereby forming a desired silver halide emulsion for use in the present invention.

Typical known high-boiling solvents include phthalate esters (e.g. phthalate dibutyl and dioctyl phthalate), phosphate esters (e.g. tricresyl phosphate and trioctyl phosphate) and N-substituted acid amides (e.g. N,N-diethyllaurylamide).

Some of the phenolic compounds of the present invention may be used as high-boiling solvents per se, and compounds (2), (3), (6), (10) and (21) are examples of this group. If these compounds are used, other high-boiling solvents such as phthalate esters need not be used. The phenolic compound of the present invention may be dispersed separately from the magenta coupler of the present invention, and the two are individually added to the same silver halide emulsion. Preferably, the two are dissolved and added in the silver halide emulsion simultaneously.

For incorporation in the silver halide emulsion, the magenta coupler according to the present invention is used in an amount which generally ranges from about 0.01 to 2 mols, preferably from 0.03 to 0.5 mol, per mol of silver halide.

The greater the amount of the phenolic compound of the present invention that is used in comparison with the magenta coupler of the present invention, the more favorable it is to the objects of the present invention. Stated more specifically, the phenolic compound of the present invention is used in an amount of 0.1 to 10 g, preferably 0.25 to 3 g, per gram of the magenta coupler of the present invention.

The silver halide used in the silver halide emulsion according to the present invention is selected from among any of those which are used in conventional silver halide emulsions, such as silver bromide, silver chloride, silver iodobromide, silver chlorobromide and silver chloroiodobromide.

The silver halide emulsions making up the silver halide emulsion layers according to the present invention may be prepared by any of the common techniques. A typical example is shown in Japanese Patent Publication No. 7772/1971 and concerns the production of a "conversion emulsion": an emulsion of silver salt particles at least part of which has a higher solubility than silver bromide is first prepared, and then, at least part of these grains is converted to silver bromide or silver iodobromide. Alternatively, the method for preparing a Lippmann emulsion composed of fine silver halide grains having an average size of 0.1 μm or less may be employed.

The silver halide emulsions according to the present invention may be chemically sensitized by a sulfur sensitizer (e.g. arylthiocarbamide, thiourea or cystine), an active or inactive selenium sensitizer, a reduction sensitizer (e.g. stannous salt or polyamine), a noble metal sensitizer such as a gold sensitizer (e.g. potassium aurithiocyanate, potassium chloroaurate or 2-aurosulfobenzothiazole methyl chloride) or a water-soluble salt of ruthenium, rhodium or iridium (e.g. ammonium chloropalladate, potassium chloroplatinate or sodium chloropalladite). These chemical sensitizers may be used either alone or in combination.

The silver halide emulsions used in the present invention may contain various known photographic additives, such as those shown in Research Disclosure, December 1978, No. 17643.

The silver halide used in the present invention may be spectrally sensitized with a suitable sensitizing dye for the purpose of affording sensitivity to the necessary wavelength range. Various spectral sensitizers may be employed either alone or in combination. Those which are used with advantage in the present invention are cyanine dyes, merocyanine dyes or complex cyanine dyes of the types shown in U.S. Pat. Nos. 2,269,234, 2,270,378, 2,442,710, 2,454,620 and 2,776,280.

The support used in the present invention may be properly selected from among known materials depending upon the specific type of the photographic material used, and suitable support materials are plastic films, plastic-laminated paper, baryta paper, and synthetic paper. These supports are generally subbed to provide a stronger adhesion to a photographic emulsion layer.

The silver halide color photographic material of the present invention shown above is exposed and subjected to various methods of color development. A color developer preferably used in processing the photographic material of the present invention contains an aromatic primary amine color developing agent as the main component. Typical color developing agents are p-phenylenediamine compounds, such as diethyl-p-phenylenediamine hydrochloride, monomethyl-p-phenylenediamine hydrochloride, dimethyl-p-phenylenediaminehydrochloride, 2-amino-5-diethylaminotoluene hydrochloride, 2-amino-5-(N-ethyl-N-dodecylamino)-toluene, 2-amino-5-(N-ethyl-N-β-methanesulfonamidoethyl)aminotoluene sulfate, 4-(N-ethyl-N-β-methanesulfonamidoethylamino)aniline, 4-(N-ethyl-N-β-hydroxyethylamino)aniline, and 2-amino-5-(N-ethyl-β-methoxyethyl)aminotoluene. These color developing agents may be used either alone or in combination with themselves. They may also be used in black-and-white developing agents such as hydroquinone. The color developing solutions used in the present invention generally contain an alkali agent such as sodium hydroxide, ammonium hydroxide, sodium carbonate or sodium sulfite, as well as other additives such as an alkali metal halide (e.g. potassium bromide) and a development regulator (e.g. hydrazine acid).

The silver halide color photographic material of the present invention may contain the color developing agent in a hydrophilic colloidal layer in the form of its precursor. A precursor of the color developing agent is a compound that is capable of producing the developing agent under alkaline conditions illustrative precursors are Schiff base precursors with aromatic aldehyde derivatives, polyvalent metallic ion complex precursors, phthalimide derivative precursors, phosphamide derivative precursors, sugar-amine reaction product precursors, and urethane precursors. Illustrative precursors for the aromatic primary color developing agent are shown in U.S. Pat. Nos. 3,342,599, 2,507,114, 2,695,234, 3,719,492, British Pat. No. 803,783, Japanese Patent Public Disclosure Nos. 135628/1978, 79035/1979, Research Disclosure Nos. 15,159, 12,146 and 13,924.

The aromatic primary amine color developing agents or their precursors shown above must be present in amounts sufficient to provide the desired color as a result of color development. The necessary amount varies significantly depending upon the type of the photographic material to be processed, and generally, it ranges from 0.1 mol to 5 mols, preferably from 0.5 mol to 3 mols, per mol of light-sensitive silver halide. The color developing agents or their precursors may be used either alone or in combination. These compounds may be incorporated in the photographic material either by dissolving them in a suitable solvent such as water, methanol, ethanol or acetone, or by using an emulsion in a high-boiling solvent such as dibutyl phthalate, dioctyl phthalate or tricresyl phosphate. If desired, the compounds may be impregnated in a latex polymer as shown in Research Disclosure No. 14850.

After color development, the silver halide color photographic material of the present invention is bleached, fixed and washed with water. The steps of bleaching and fixing may be performed simultaneously as a bleach-fixing step. While many compounds may be used as bleaching agents, compounds of polyvalent metals such as iron(III), cobalt(III) and tin(II) are preferably used. Particularly preferred compounds are complex salts of these polyvalent metallic cations and organic acids such as aminopolycarboxylic acids (e.g. ethylenediaminetetraacetic acid, nitrilotriacetic acid, and N-hydroxyethylenediaminediacetic acid), or organic acids (e.g. malonic acid, tartatic acid, malic acid, diglycolic acid and dithioglycolic acid). Alternatively, ferricyanates and bichromates may be used. These bleaching compounds may be used either alone or in combination.

By using the magenta coupler of the present invention in combination with the phenolic compound of the present invention, the present invention provides a silver halide color photographic material which has high sensitivity and forms a magenta dye exhibiting high color density. This photographic material remains highly stable in the presence of a deleterious substance in the air, such as formalin. Furthermore, the silver halide color photographic material of the present invention forms a magenta dye which does not have any absorption other than the principal adsorption that is not desired, and therefore, said material provides good color reproduction. As other advantages, the photographic material of the present invention has high sensitivity and exhibits high color forming ability, and this makes it possible to reduce the necessary amount of the coupler, silver deposit, as well as the amount of gelatin, oils and other additives used. As a result, not only is the thickness of the emulsion layers reduced but also better sharpness can be provided to the underlying layers.

SPECIFIC EMBODIMENTS OF THE INVENTION

The present invention is hereunder described in greater detail by reference to working examples, to which the possible embodiments of the present invention are by no means limited.

EXAMPLE 1

The magenta couplers shown in Table 1 (three of which were according to the present invention, and the other four were comparative samples) were used. A tenth of a mole of each coupler per mol of silver was dissolved in an equal amount, by weight, of tricresyl phosphate, a suitable amount of the phenolic compound of the present invention, and three times the weight of the coupler of ethyl acetate. The mixture was heated at 60° C. to obtain a complete solution. The solution was mixed with 1200 ml of a 5% aqueous gelatin solution containing 120 ml of a 5% aqueous solution of Alkanol B (alkyl naphthalenesulfonate, a product of E. I. du Pont de Nemours & Co.), and an emulsion was prepared from the mixture by treatment with an ultrasonic disperser. The dispersion was mixed with 4 kg of a green-sensitive silver iodobromide emulsion (containing 6 mol of silver iodide) in the presence of 120 ml of a hardener, or 2% solution of 1,2-bis(vinylsulfonyl)ethane in water/methanol (1:1). The mixture was applied to a subbed transparent polyester base and the web was dried. By this procedure, samples 1 to 26 of silver halide photographic material were prepared. In all samples, the silver deposit was 20 mg/100 cm$^2$.

The samples thus prepared were exposed to light through a wedge by the conventional method and processed according to the following scheme. The results are shown in Table 1.

| Processing (38° C.) | Time |
|---|---|
| Color development | 3 min 15 sec |
| Bleaching | 1 min 30 sec |
| Washing | 3 min 15 sec |
| Fixing | 6 min 30 sec |
| Washing | 3 min 15 sec |
| Stabilizing | 1 min 30 sec |

The solutions used in the respective processing steps had the following formulations.

| Components | Amount (g) |
|---|---|
| Color developer | |
| 4-Amino-3-methyl-N—ethyl-N—(β-hydroxyethyl)-aniline sulfate | 4.75 |
| Anhydrous sodium sulfite | 4.25 |
| Hydroxylamine hemisulfate | 2.0 |
| Anhydrous potassium carbonate | 37.5 |
| Sodium bromide | 1.3 |
| Nitrilotriacetic acid trisodium salt (monohydrate) | 2.5 |
| Potassium hydroxide | 1.0 |
| Water to make | 1,000 ml |
| pH adjusted to 10.0 with KOH | |
| Bleaching solution | |
| Ethylenediaminetetraacetic acid iron ammonium salt | 100.0 g |
| Ethylenediaminetetraacetic acid diammonium salt | 10.0 g |
| Ammonium bromide | 150.0 g |
| Glacial acetic acid | 10.0 ml |
| Water to make | 1,000 ml |
| pH adjusted to 6.0 with ammonia water | |
| Fixing solution | |
| Ammonium thiosulfate (50% aq. sol.) | 162 ml |
| Anhydrous sodium sulfite | 12.4 ml |
| Water to make | 1,000 ml |
| pH adjusted to 6.5 with acetic acid | |
| Stabilizing bath | |
| Formalin (37% aq. sol.) | 5.0 ml |
| Konidax (product of Konishiroku Photo Industry Co., Ltd.) | 7.5 ml |
| Water to make | 1,000 ml |

TABLE 1

| Sample No. | Coupler | HBS *1 | Phenolic compound of the present invention No. | Amount *2 | Specific Sensitivity *3 | Maximum Density | Formalin Resistance *4 | Maximum Spectral Absorption (λ max) *5 |
|---|---|---|---|---|---|---|---|---|
| 1 | Comparative | o | — | — | 100 | 2.07 | 50 | 554 |

TABLE 1-continued

| | Coupler | *1 | *2 | | *3 | | *4 | *5 |
|---|---|---|---|---|---|---|---|---|
| 2 | Comparative Coupler 1 | — | 8 | 1.0 | 112 | 2.25 | 53 | 561 |
| 3 | Comparative Coupler 2 | o | — | — | 230 | 2.88 | 56 | 551 |
| 4 | Comparative Coupler 2 | — | 8 | 1.0 | 240 | 2.92 | 57 | 555 |
| 5 | Comparative Coupler 3 | o | — | — | 150 | 3.00 | 85 | 545 |
| 6 | Comparative Coupler 3 | — | 8 | 1.0 | 200 | 3.10 | 86 | 549 |
| 7 | Comparative Coupler 4 | o | — | — | 85 | 2.50 | 81 | 546 |
| 8 | Comparative Coupler 4 | — | 8 | 1.0 | 100 | 2.83 | 87 | 552 |
| 9 | Comparative Coupler 5 | o | — | — | 130 | 3.40 | 95 | 552 |
| 10 | Comparative Coupler 5 | — | 8 | 1.0 | 180 | 3.65 | 94 | 559 |
| 11 | M - 6 | o | — | — | 200 | 3.10 | 91 | 546 |
| 12 | M - 2 | — | 6 | 1.0 | 284 | 3.84 | 92 | 553 |
| 13 | M - 2 | o | 19 | 0.5 | 270 | 3.65 | 93 | 551 |
| 14 | M - 2 | — | 3 | 1.0 | 273 | 3.75 | 92 | 552 |
| 15 | M - 6 | — | 6 | 1.0 | 232 | 3.70 | 90 | 553 |
| 16 | M - 6 | — | 21 | 1.0 | 240 | 3.80 | 91 | 553 |
| 17 | M - 6 | o | 7 | 0.5 | 220 | 3.50 | 92 | 550 |
| 18 | M - 7 | o | 5 | 1.0 | 230 | 3.92 | 92 | 554 |
| 19 | M - 7 | — | 3 | 1.0 | 236 | 3.95 | 90 | 555 |
| 20 | M - 7 | o | 26 | 0.5 | 220 | 3.85 | 91 | 552 |
| 21 | M - 13 | — | 6 | 1.0 | 289 | 4.10 | 91 | 553 |
| 22 | M - 13 | o | 19 | 0.5 | 280 | 4.05 | 91 | 553 |
| 23 | M - 13 | o | 12 | 0.7 | 282 | 3.99 | 92 | 552 |
| 24 | M - 16 | — | 6 | 1.0 | 220 | 3.45 | 90 | 552 |
| 25 | M - 16 | — | 11 | 1.0 | 215 | 3.30 | 92 | 551 |
| 26 | M - 16 | o | 16 | 0.5 | 210 | 3.30 | 91 | 550 |

*1: HBS indicates tricresyl phosphate.
The symbol (—) means the non-use of HBS and (o) means its use.

*2: The amount of the phenolic compound of the present invention used is indicated in terms of the relative value given by:

$$\frac{\text{Weight of phenolic compound}}{\text{Weight of coupler}}$$

*3: The specific sensitivity is the reciprocal of exposure that gave a density equal to fog + 0.1.
The data on specific sensitivity is based on relative values, with the value for comparative coupler 1 being taken as 100.

*4: Before color development, each sample was held in a closed vessel (30° C., 62% rh) containing 6 cc of 0.9% formalin for 3 days. As a control, a sample that was not treated with formalin was developed.
The formalin resistance was calculated by the following formula:

$$\text{Formalin resistance} = \frac{\text{Color density of formalin-treated sample}}{\text{Color density of untreated sample}} \times 100\ (\%)$$

*5: The maximum spectral absorption was the wavelength in nm of the peak absorption of a color developed sample for a density of 1.0.

Comparative coupler 1:

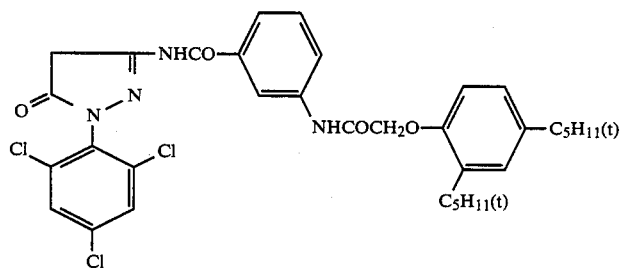

Comparative coupler 2 (as shown in Japanese Patent Publication No. 16058/1974):

TABLE 1-continued

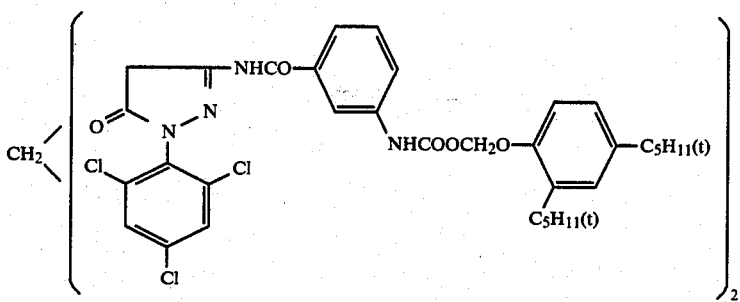

Comparative coupler 3 (as shown in Japanese Patent Publication No. 30895/1973):

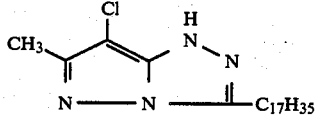

Comparative coupler 4 (as shown in Japanese Patent Public Disclosure No. 135841/1981):

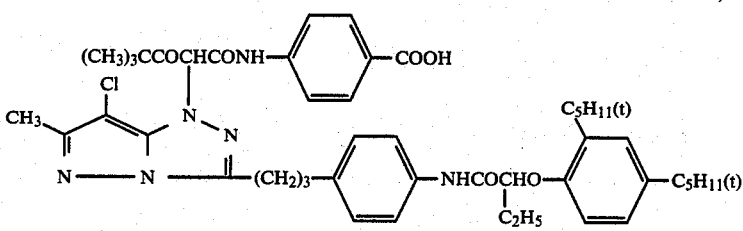

Comparative coupler 5 (as shown in Japanese Patent Public Disclosure No. 42045/1983):

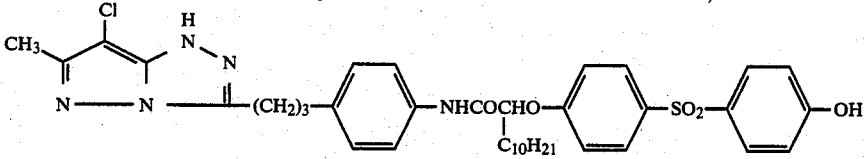

As Table 1 shows, comparative coupler 1 which has hitherto been put to practical use exhibited unsatisfactory results with respect to sensitivity, maximum density and formalin resistance. Some improvement was achieved by additionally using the phenolic compound of the present invention, but the degree of the improvement was not what was intended by the present inventors. Comparative coupler 2 had an improved sensitivity, but the maximum color density and formalin resistance achieved by this coupler were low and could not be substantially improved by adding the phenolic compound of the present invention. Comparative coupler 3 provided some improvement in the formalin resistance, as well as in the sensitivity and maximum color density, but the improvement was far from being satisfactory. Comparative coupler 4 had some improvement in the formalin resistance, but it did not give any good results with sensitivity nor maximum color density, and no significant improvement in these respects was obtainable by adding the phenolic compound of the present invention. Comparative coupler 5 achieved a great improvement in both the maximum color density and formalin resistance, but its sensitivity performance was insufficient and could not be substantially improved by adding the phenolic compound. Coupler M-6 which was contemplated by a previous application filed by the present inventors had a certain degree of improvement in sensitivity, maximum color density and formalin resistance, but in the absence of the phenolic compound of the present invention, the improvement was not as great as the inventors expected. Another defect was its sensitivity to shorter wavelengths.

By using the coupler of the present invention in combination with the phenolic compound of the present invention, silver halide color photograhic materials that have maximum color density and formalin resistance comparable to or higher than those achieved by Comparative coupler 5 and which provide a significantly improved sensitivity and form a magenta dye having desired spectral absorption characteristics can be produced.

EXAMPLE 2

The magenta couplers according to the present invention that are shown in Table 2 were used. A tenth of a mole of each coupler per mol of silver was dissolved in an equal amount, by weight of 2,4-di-tert-amylphenol of the same weight as each coupler and three times the weight of the coupler of ethyl acetate.

The mixture was heated at 60° C. to obtain a complete solution. The solution was mixed with 1200 ml of a 5% aqueous gelatin solution containing 120 ml of a 5% aqueous solution of Alkanol B (alkyl naphthalenesulfonate, a product of E. I. Du Pont de Nemours & Co.), and an emulsion was prepared from the mixture by treatment with an ultrasonic disperser. The dispersion was mixed with 4 kg of a green-sensitive silver iodobromide emulsion (containing 6 mol of silver iodide) in the presence of 120 ml of a hardener, or 2% solution of 1,2-bis(vinylsulfonyl)ethane in water/methanol (1:1). The mixture was applied to a subbed transparent polyester base and the web was dried.

The Samples Nos. 1, 3, 5 and 7 used in Example 1 were also used for comparison. The samples thus prepared were exposed to light through a wedge by the conventional method and processed in the same manner as in Example 1.

TABLE 2

| Sample No. | Coupler | HBS *6 | Amount of Silver (mg/100 cm²) | Specific Sensitivity | Maximum Density |
|---|---|---|---|---|---|
| 1 | Comparative Coupler 1 | TCP | 20 | 100 | 2.07 |
| 3 | Comparative Coupler 2 | " | " | 230 | 2.88 |
| 5 | Comparative Coupler 3 | " | " | 150 | 3.00 |
| 7 | Comparative Coupler 4 | " | " | 85 | 2.50 |
| 27 | M-1 | DAP | 10 | 110 | 2.81 |
| 28 | M-2 | " | " | 140 | 2.95 |
| 29 | M-4 | " | " | 120 | 2.90 |
| 30 | M-6 | " | " | 115 | 3.04 |
| 31 | M-7 | " | " | 145 | 3.10 |
| 32 | M-9 | " | " | 185 | 3.30 |
| 33 | M-13 | " | " | 190 | 3.35 |
| 34 | M-16 | " | " | 115 | 2.92 |
| 35 | M-20 | " | " | 110 | 2.85 |

*6 TCP represents tricresyl phosphate, and DAP 2,4-di-tert-amylphenol.

As Table 2 shows, the samples using the coupler and phenolic compound according to the present invention required half the amount of the silver that was deposited in the comparative samples. Nevertheless, these samples exhibited sensitivity and maximum color density which were comparable to or higher than those achieved by the comparative couplers. This suggests the improved efficiency in the use of silver halide that is attained by using the coupler of the present invention in combination with the phenolic compound of the present invention. As one can see, this combination provides a photographic material that fully satisfies the objects of the present invention by reducing the required amount of silver deposit, hence the thickness of the individual silver halide emulsion layers, and by providing improved sharpness to the underlying layers.

As will be readily understood from Examples 1 and 2, by using the magenta coupler of the present invention in combination with the phenolic compound of the present invention, a silver halide color photographic material having a stable color balance can be prepared by applying to a transparent support a blue-sensitive silver halide emulsion layer containing an open-chain active methylene yellow coupler, a green-sensitive silver halide emulsion layer containing the magenta coupler of the present invention, and a red-sensitive silver halide emulsion layer containing a phenolic or naphtholic cyan coupler, each emulsion layer containing suitable photographic additives and being applied by a conventional technique.

What is claimed is:

1. A silver halide color photographic material having at least one silver halide emulsion layer on a support, said silver halide emulsion layer containing at least one magenta coupler of formula (I) and at least one non-color forming phenolic compound:

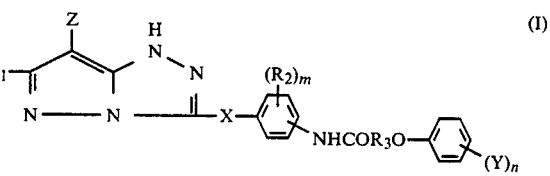

wherein $R_1$ is an alkyl or aryl group; $R_2$ is a monovalent group; $R_3$ is an alkylene group; Y is a halogen atom, a hydroxy or alkyl group; Z is a group that can be eliminated upon coupling reaction with the oxidized product of a color developing agent; X is a divalent bonding group or an alkylene group having 1 to 5 carbon atoms; m is an integer of 0 to 4; and n is an integer of 0 to 5.

2. A silver halide color photographic material according to claim 1, wherein said non-color forming phenolic compound is represented by the following formula (II):

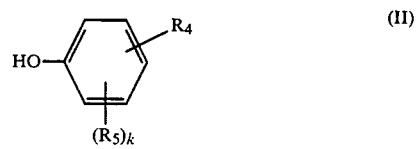

wherein $R_4$ and $R_5$ are each a halogen atom, an alkyl group, a cycloalkyl group or an alkoxy group; and k is an integer of 0 to 4, provided that when k is 2 or more, $R_5$ may be the same or different groups.

3. A silver halide color photographic material according to claim 1, wherein x in said formula (I) is —CH$_2$)$_l$ (wherein l is an integer of 1 to 5).

4. A silver halide color photographic material according to claim 2, wherein k in said formula (II) is 0 or 1.

5. A silver halide color photographic material according to claim 1, wherein the monovalent group represented by $R_2$ in said formula (I) is a group selected from among a halogen atom and alkoxy, alkyl, nitro and cyano groups.

6. A silver halide color photographic material according to claim 2, wherein the alkyl group represented by each of $R_4$ and $R_5$ in said formula (II) has 1 to 20 carbon atoms.

7. A silver halide color photographic material according to claim 2, wherein the alkyl group represented by each of $R_4$ and $R_5$ in said formula (II) has 1 to 10 carbon atoms.

8. A silver halide color photographic material according to claim 1, wherein the alkyl group represented by $R_1$ in said formula (I) has 1 to 8 carbon atoms.

* * * * *